United States Patent
Lewallen

(10) Patent No.: US 10,310,558 B2
(45) Date of Patent: Jun. 4, 2019

(54) APPARATUS AND METHOD FOR COMPUTING NODE AND SEAT CONNECTION FOR CONDUCTIVE FABRIC

(71) Applicant: Intel Corporation, Santa Clara, CA (US)

(72) Inventor: Eric Lewallen, Portland, OR (US)

(73) Assignee: Intel Corporation, Santa Clara, CA (US)

(*) Notice: Subject to any disclaimer, the term of this patent is extended or adjusted under 35 U.S.C. 154(b) by 0 days.

(21) Appl. No.: 15/496,512

(22) Filed: Apr. 25, 2017

(65) Prior Publication Data

US 2018/0307267 A1    Oct. 25, 2018

(51) Int. Cl.
| | | |
|---|---|---|
| G06F 1/16 | (2006.01) | |
| A61B 5/00 | (2006.01) | |
| A61B 5/11 | (2006.01) | |
| E04H 15/54 | (2006.01) | |

(52) U.S. Cl.
CPC ............ *G06F 1/163* (2013.01); *A61B 5/1118* (2013.01); *A61B 5/6804* (2013.01); *E04H 15/54* (2013.01); *G06F 1/1656* (2013.01)

(58) Field of Classification Search
None
See application file for complete search history.

(56) References Cited

U.S. PATENT DOCUMENTS

| | | | | |
|---|---|---|---|---|
| 7,206,630 B1* | 4/2007 | Tarler | ................... | A61B 5/0006 600/509 |
| 2002/0076948 A1* | 6/2002 | Farrell | ...................... | B32B 3/08 438/800 |
| 2002/0124295 A1* | 9/2002 | Fenwick | ............ | A41D 13/1245 2/69 |
| 2007/0285868 A1* | 12/2007 | Lindberg | ............. | A61B 5/0245 600/382 |

(Continued)

FOREIGN PATENT DOCUMENTS

KR    101570875 B1    12/2015

OTHER PUBLICATIONS

Rachel Babbage ( Jan. 9, 2016) These Samsung smart clothes connect every single part of your body to an app, retrieved from URL <<http://www.digitalspy.com/tech/ces/news/a779412/these-samsung-smart-clothes-connect-very-single-part-of-your-body-to-an-app/>> [Mar. 24, 2017 11:37:19 AM].

*Primary Examiner* — Courtney L Smith
*Assistant Examiner* — Rashen E Morrison
(74) *Attorney, Agent, or Firm* — Schwabe, Williamson & Wyatt, P.C.

(57) ABSTRACT

The present disclosure describes a number of embodiments related to a fabric having one or more embedded wires, with the computer node integrated into the fabric that has a base conductive fabric and one or more system leads coupled to the base conductive fabric to electrically couple a computer node removably seated in the computer node seat with one or more embedded wires in the fabric, where the computer (Continued)

node seat has a thickness or a flexibility substantially similar to the fabric and is substantially flat. In other embodiments, the computer node may include a single housing or double housing and may attach to the computer node seat such that a portion of the computer node is disposed both above and below a plane of the computer node seat.

17 Claims, 6 Drawing Sheets

(56) References Cited

U.S. PATENT DOCUMENTS

| | | | |
|---|---|---|---|
| 2010/0198043 A1* | 8/2010 | Holzer | A41D 13/1281 600/388 |
| 2013/0160183 A1* | 6/2013 | Reho | A41D 13/1281 2/69 |
| 2013/0274587 A1* | 10/2013 | Coza | A61B 5/6804 600/409 |
| 2013/0321168 A1* | 12/2013 | Mahony | A61B 5/002 340/870.09 |
| 2014/0090146 A1* | 4/2014 | Yeomans | A41D 1/002 2/69 |
| 2015/0331524 A1* | 11/2015 | McMillen | G01L 1/18 345/174 |
| 2015/0331533 A1* | 11/2015 | McMillen | G06F 1/16 345/174 |
| 2016/0058076 A1 | 3/2016 | Reho et al. | |
| 2016/0181729 A1* | 6/2016 | Barth | A41D 1/005 439/37 |
| 2016/0270727 A1* | 9/2016 | Berg | A61B 5/7203 |
| 2017/0332442 A1* | 11/2017 | Strecker | A41D 13/0051 |

\* cited by examiner

APPARATUS AND METHOD FOR COMPUTING NODE AND SEAT CONNECTION FOR CONDUCTIVE FABRIC

FIELD

Embodiments of the present disclosure generally relate to the field of wearable computing or smart garments. More specifically, embodiments of the present disclosure may relate to removable computing nodes and computing node seats integrated into garment fabrics, to receive the computing nodes.

BACKGROUND

Smart garments consist of wearable sensors that are integrated directly into fabric with conductive traces leading to a removable computing or hub device. Hub connections in removable arrangements are typically achieved via two or more conductive snap connectors or a pocket sewn into the garment and a wired connection, allowing the computing/hub device to be removed prior to washing the garment. There exists the need for secure attachment methods and mechanism that enable design flexibility and more integrated designs that are not achievable using multiple snap connectors or pockets. Legacy fabric-integrated computing devices rely on metal snap connectors to enable robust electrical connections between a processing node and a fabric-based sensing system.

BRIEF DESCRIPTION OF THE DRAWINGS

Embodiments will be readily understood by the following detailed description in conjunction with the accompanying drawings. To facilitate this description, like reference numerals designate like structural elements. Embodiments are illustrated by way of example and not by way of limitation in the figures of the accompanying drawings.

DETAILED DESCRIPTION

Figure 1:
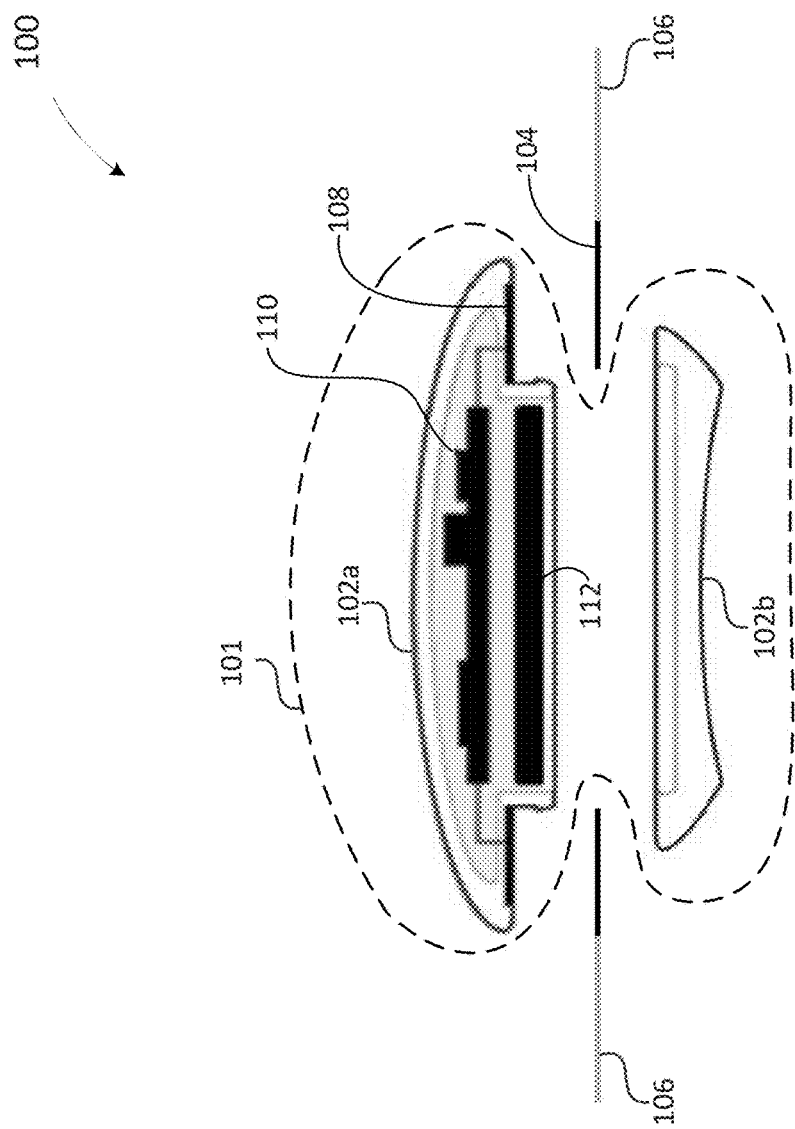
FIG. 1 is a diagram of a separable computing node removably embedded into a computing node seat attached to a fabric, in accordance with some embodiments.

As new lightweight electronic components with smaller embedded profiles continue to be developed, there may be an advantage for new connectors that can expand the design options for smart garment apparel or other smart fabric-based applications. These new connectors may enable a lower-profile component to be attached and detached in a smooth way to prevent damage to circuitry within the component.

In embodiments, the apparatus, system, and/or processes to implement such electronic components within smart garments may include two components: a small, encapsulated computing node for processing having a connector base, and a conductive computing node seat that may be integrated into the smart fabric. In embodiments, the computing node may house the processor, electronics, battery, and physical connectors that may attach directly to the computing node seat. The computing node seat may be permanently bonded to the garment fabric and may provide a stable conductive base for connecting the computing node through the computing node seat to the fabric sensing system of a smart garment.

In embodiments, the computing node may be attached to a fabric-based electrical system without the use of legacy connectors such as hard metal snap connectors or a specially designed fabric pockets within a garment fabric. In embodiments, the computing node may be twist-embedded into a computing node seat, which may enable a lower visual profile and the perception of a smaller device in the fabric by distributing the thickness, or z-height, of the computing node between the front and back sides of the computing node seat and/or fabric. In embodiments, the fabric may be a garment fabric that may be worn, or may be some other type of fabric such as a tent, awning, or other covering. The fabric may be referred to as a fabric article. These terms may be used interchangeably herein. In embodiments, the fabric may include a cloth fabric.

In embodiments, a computing node and/or computing node seat may enable stable electronics integration into very thin fabrics, for example, Lycra™ or other stretchable knit fabric structures. In embodiments, sensing data from sensors located in or proximate to the fabric may also be drawn out from the underside of the fabric. For example, sensors in the garment fabric may maintain direct contact with the wearer's skin as a component of a smart garment bio-sensing system that may directly measure body temperature, sweat, or other factors.

In embodiments, the computing node seat may include a hole that may be used to facilitate seating of a computing node. The hole may also be within the garment fabric proximate to the computing node seat. In embodiments, the computing node seat may be reinforced with a semi-rigid bonded material such as Bemis Exoflex™ film, which may provide a stable base for the computing node seat and the conductive pathways leading from the computing node seat. The conductive pathways may pass through the garment fabric via slits or holes to enable connection with a sensing system of which the computing node may be a part.

In embodiments, the computing node may consist of two halves, a first housing which may be a top cap and a second housing which may be a bottom threaded base. The first housing and the second housing may be fitted together to form a complete computing node unit. In embodiments, portions of the computing node seat and/or garment fabric may be disposed between the first and the second housing. In embodiments, when fitted together a small gap may remain between the two halves, and may allow space for the garment fabric between the two halves. Electrical contacts may be positioned within this gap; which may enable a secure connection and/or electrical coupling to the conductive paths within the garment. In embodiments, the two halves may be secured by twisting them together, by snapping them together, by interlocking them together, or by securing them in some other suitable manner so that they may be in alignment with the electrical contact points of the computing node and the computing node seat.

In embodiments, the computing node may be attached to the garment by inserting the computing node into the computing node seat and twisting along the threaded base until the computing node is fully threaded into the computing node seat, at which point the electrical connection between the node and garment fabric may be aligned to enable a secure electrical coupling. In embodiments, the number of contact points between the computing node and the computing node seat may vary depending on the application.

In embodiments, the computing node and/or the computing node seat may be referred to as a computer node and/or a computer node seat.

In the following description, various aspects of the illustrative implementations are described using terms commonly employed by those skilled in the art to convey the substance of their work to others skilled in the art. However, it will be apparent to those skilled in the art that embodiments of the present disclosure may be practiced with only some of the described aspects. For purposes of explanation, specific numbers, materials, and configurations are set forth in order to provide a thorough understanding of the illustrative implementations. However, it will be apparent to one skilled in the art that embodiments of the present disclosure may be practiced without the specific details. In other instances, well-known features are omitted or simplified in order not to obscure the illustrative implementations.

In the following description, reference is made to the accompanying drawings that form a part hereof, wherein like numerals designate like parts throughout, and in which is shown by way of illustration embodiments in which the subject matter of the present disclosure may be practiced. It is to be understood that other embodiments may be utilized and structural or logical changes may be made without departing from the scope of the present disclosure. Therefore, the following detailed description is not to be taken in a limiting sense, and the scope of embodiments is defined by the appended claims and their equivalents.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B, and C).

The description may use perspective-based descriptions such as top/bottom, in/out, over/under, and the like. Such descriptions are merely used to facilitate the discussion and are not intended to restrict the application of embodiments described herein to any particular orientation.

The description may use the phrases "in an embodiment," or "in embodiments," which may each refer to one or more of the same or different embodiments. Furthermore, the terms "including," "having," and the like, as used with respect to embodiments of the present disclosure, are synonymous. The term smart garment/fabric as used herein refers to a garmet/fabric having integrated or removably embedded computing and/or sensing capabilities.

The terms "coupled with" and "coupled to" and the like may be used herein. "Coupled" may mean one or more of the following. "Coupled" may mean that two or more elements are in direct physical or electrical contact. However, "coupled" may also mean that two or more elements indirectly contact each other, but yet still cooperate or interact with each other, and may mean that one or more other elements are coupled or connected between the elements that are said to be coupled with each other. By way of example and not limitation, "coupled" may mean two or more elements or devices are coupled by electrical connections on a printed circuit board such as a motherboard, for example. By way of example and not limitation, "coupled" may mean two or more elements/devices cooperate and/or interact through one or more network linkages such as wired and/or wireless networks. By way of example and not limitation, a computing apparatus may include two or more computing devices "coupled" on a motherboard or by one or more network linkages.

Various operations are described as multiple discrete operations in turn, in a manner that is most helpful in understanding the claimed subject matter. However, the order of description should not be construed as to imply that these operations are necessarily order dependent.

FIG. 1 is a diagram of a separable computing node removably embedded into a computing node seat attached to a fabric, in accordance with some embodiments. Diagram 100 may include a computing node 101 that may include a first housing 102a and a second housing 102b that may be secured to a computing node seat 104. In embodiments the computing node seat 104, described in more detail in FIGS. 3 and 4, may be secured to a fabric 106. In embodiments, the fabric 106 may include conductive fabric, conductive thread, or wires (not shown) that lead to sensors (not shown) that may be contained within or proximate to the fabric 106.

In embodiments, the first housing 102a and the second housing 102b may be combined and secured to the computing node seat 104 by screwing the two housings together. In embodiments, other actions may be used to secure the housings together, for example by snapping them together or otherwise interlocking them together. In embodiments, once the housings are secured together, this may cause an electrical coupling between the computing node seat 104 and contacts 108 in the first housing 102a.

The contacts 108 within the first housing 102a may be connected to one or more electronics components 110 with the first housing 102a. Electronic components 110 may include circuitry, processors, and/or wireless communication components to allow data received from various sensors (not shown) within or proximately near the node seat 104 and/or fabric 106 to be analyzed, stored, and/or communicated to another computing device (not shown). In embodiments, the electronic components 110 may be connected to a battery 112. In embodiments, the battery 112 may be removable, or may be chargeable using induction, inductively charged, or charged using some other suitable process.

In embodiments, the first housing 102a or the second housing 102b may include one or more indicators or diagrams (not shown) on the surface of the respective housings 102a, 102b to indicate where the node 101 is to be secured relative to the computing node seat 104.

In embodiments, connecting the first housing 102a or the second housing 102b by screwing them together on opposite sides of the computing node seat 104 may result in a lower profile with respect to the garment fabric and may also result in a lower impact or lower physical shock to the electronic components 110 as compared to a clip or a snap fastening. Lower impact to the electronic components 110 may result in increased reliability and availability of the electronics components 110 in the computing node 101. In embodiments, one or more of the elements associated with the first housing 102a may be included in the second housing 102b.

In embodiments, the computing node 101 may include one or more sensors (not shown) that may generate data based upon properties and/or characteristics of objects that may be proximate to the computing node 101. In embodiments, portions of the one or more sensors may be included in the first housing 102a, the second housing 102b, and/or both.

In embodiments, the computing node 101 may receive data in the form of electronic signals from one or more sensors that may be in the computing node 101, in the computing node seat 104, or in the fabric 106. In embodiments, the computing node 101 may be a special purpose computing device that, when integrated into and connected to a smart fabric, may serve as a decorative piece of a garment as well as serving as a hub and/or processor to receive data from one or more of the sensors embedded in the smart fabric.

In embodiments, the sensors embedded in the smart fabric may be used to determine human biosignals, for example levels of sweat, body temperature, heart rate, blood oxygen levels, body chemical composition, and the like. Environmental sensors may be used to determine relative humidity, ambient air temperature and the presence of chemicals or gasses. Sensors may be used to determine user location or proximity in relation to other connected devices. Sensors with an inertial measurement unit (IMU) can detect user motion, for example running speed, running duration, acceleration, jump height, and the degree of rotation of flips or spins. Sensors may also be integrated at multiple points on the body as a kinematic system for the assessment of sport performance, good form, gait assessment, stability and balance.

Figure 2:
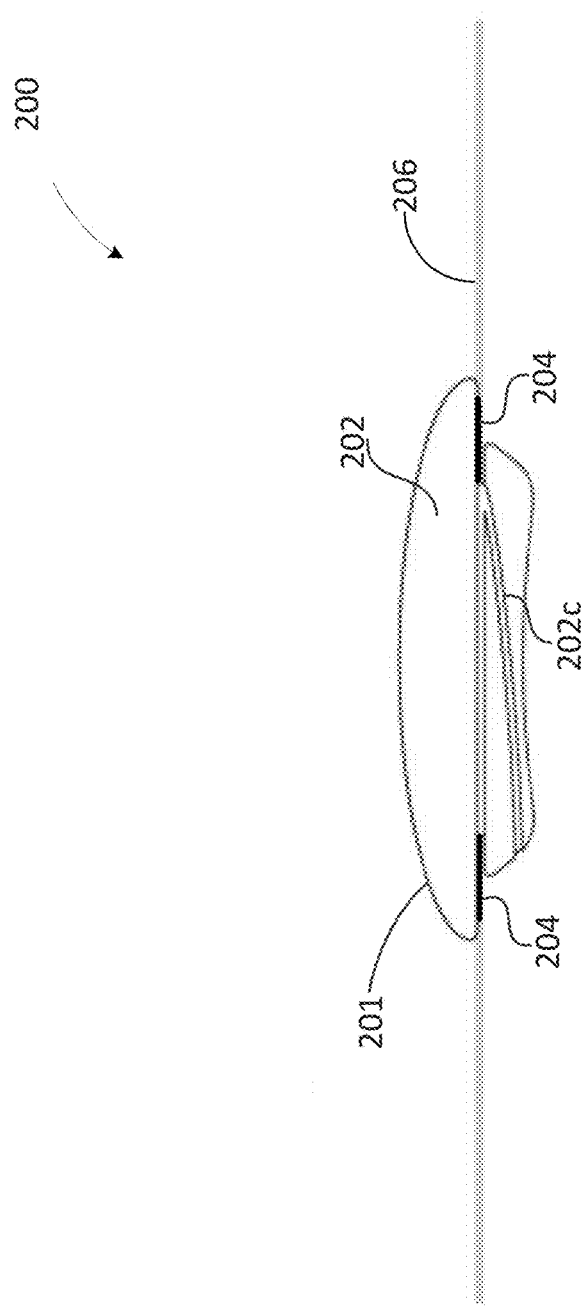
FIG. 2 is a diagram of a computing node removably embedded into a computing node seat attached to a fabric, in accordance with some embodiments.

FIG. 2 is a diagram of a computing node removably embedded into a computing node seat attached to a fabric, in accordance with some embodiments. Diagram 200 shows an embodiment of a computing node 201, which may be similar to the computing node 101 of FIG. 1. The computing node 201 may include a single housing 202 that may contain one or more of the electronic components 110 referred to in FIG. 1. The computing node 201 is shown seated into the computing node seat 204, which may be similar to the computing node seat 104 of FIG. 1. The computing node seat 204 may be integrated or otherwise coupled with the fabric 206, which may be similar to the fabric 106 of FIG. 1.

In embodiments, the housing 202 may include a threaded portion 202c that may allow the housing 202 to be screwed into a circular hole (not shown) in the node seat 204. When screwed in, the housing 202 may electrically couple with the node seat 204 using contacts 208, which may be similar to contacts 108 of FIG. 1. In embodiments, once screwed into the node seat 204, the housing 202 may be secured there by an adhesive or other sticky material (not shown) that may be a part of the computing node seat 204. In embodiments, the housing 202 around the threaded portion 202c may be a shape other than a circular shape, for examples, rectangular, elliptical, and so forth, and may screw into a hole (not shown) in the node seat 204 with a complementary geometric shape. As a result, the threaded portion 202c may tend to lock into one or more positions when the geometric shape of the threaded portion 202c and the hole (not shown) and the node seat 204 are in alignment. For example, a triangular-shaped threaded portion 202c may lock into one of three positions for a corresponding triangular-shaped hole (not shown).

In embodiments, the housing 202 may also include one or more indicators or diagrams (not shown) on the surface of the housing 202 that may be used to indicate a position and/or a desired orientation of the housing 202 in relation to the node seat 204. In embodiments these indicators may be inscriptions, etchings and/or printings on the housing 202. In embodiments, the computing node 201 may include one or more sensors (not shown) that may generate data based upon properties and/or characteristics of objects that may be proximate to the computing node 201. In embodiments, portions of the one or more sensors may be included in the housing 202.

Figure 3:
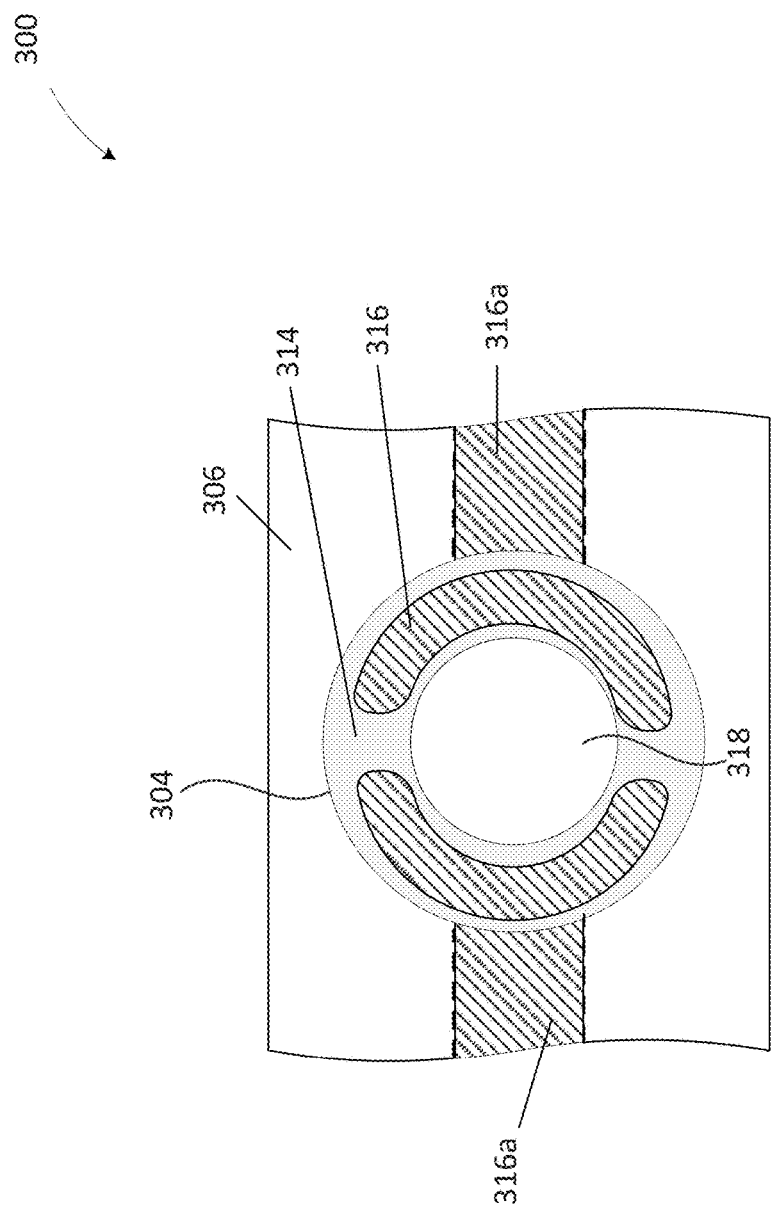
FIG. 3 is a top view of a computing node seat, in accordance with some embodiments.

FIG. 3 is a top-view of a computing node seat, in accordance with some embodiments. Diagram 300 shows a computing node seat 304, which may be similar to node seat 204 of FIG. 2 that is integrated into the fabric 306, which may be similar to fabric 206 of FIG. 2. In embodiments, the node seat 304 may be applied onto or sewn into the fabric 306. The node seat 304 may include a base conductive fabric 316 may be applied to the fabric 306. In embodiments, a base bonding material 314 may be applied onto the base conductive fabric 316, and may serve as an insulator between the base conductive fabric 316 and portions of a computing node housing (not shown) such as housing 202 of FIG. 2. In embodiments, the base bonding material 314 may have gripping or adhesive properties that may be used to secure or minimize the movement of the computing node housing 202 of FIG. 2 when it is secured to the node seat 304. In embodiments, there may be other layers that make up the node seat 304 that may be in various configurations performing various actions.

In embodiments, system leads 316a may be coupled with the base conductive fabric 316. In embodiments, one or more system leads 316a may be coupled with conductive fabric, conductive thread, or one or more wires (not shown) within fabric 306. In embodiments, there may be multiple system leads 316a that may be coupled with multiple base conductive fabrics 316 within a computing node seat 304. This may allow, for example, data from multiple sensors (not shown) or multiple zones of sensors (not shown) embedded within or proximate to the fabric 306 to be received, processed, and or transmitted by a computing node such as computing node 201 of FIG. 2. In embodiments, the system leads 316a may be on top of, in the middle of, or underneath fabric 306.

In embodiments, the computing node seat 304 may include a hole 318. As shown, the hole 318 may be a circle but, as discussed above for FIG. 2, the hole 318 may be of any shape. In embodiments, there may be no hole 318, which may instead be a base conductive fabric 316, garment fabric 306, or some other fabric (not shown). In embodiments where there is no hole 318, the computing node 101 of FIG. 1, that includes a first housing 102a and a second housing 102b may be attached (i.e. screwed together) with the garment fabric 306 between the two housings. In embodiments, one or more sensors (not shown) may be included in the computing node seat 304. The one or more sensors may provide data concerning attributes of objects proximate to the one or more sensors and may provide that data to a computing node, such as computing node 101 of FIG. 1 or 201 of FIG. 2 when seated in the computing node seat 304.

In embodiments, the computer node seat 304 may have a thickness that is substantially similar to the thickness of the fabric to which it may be coupled. In embodiments, the computer node seat 304 may have flexibility substantially similar to the flexibility of the garment fabric to which it may be coupled. In embodiments, the computer node seat 304 may be substantially flat.

Figure 4:
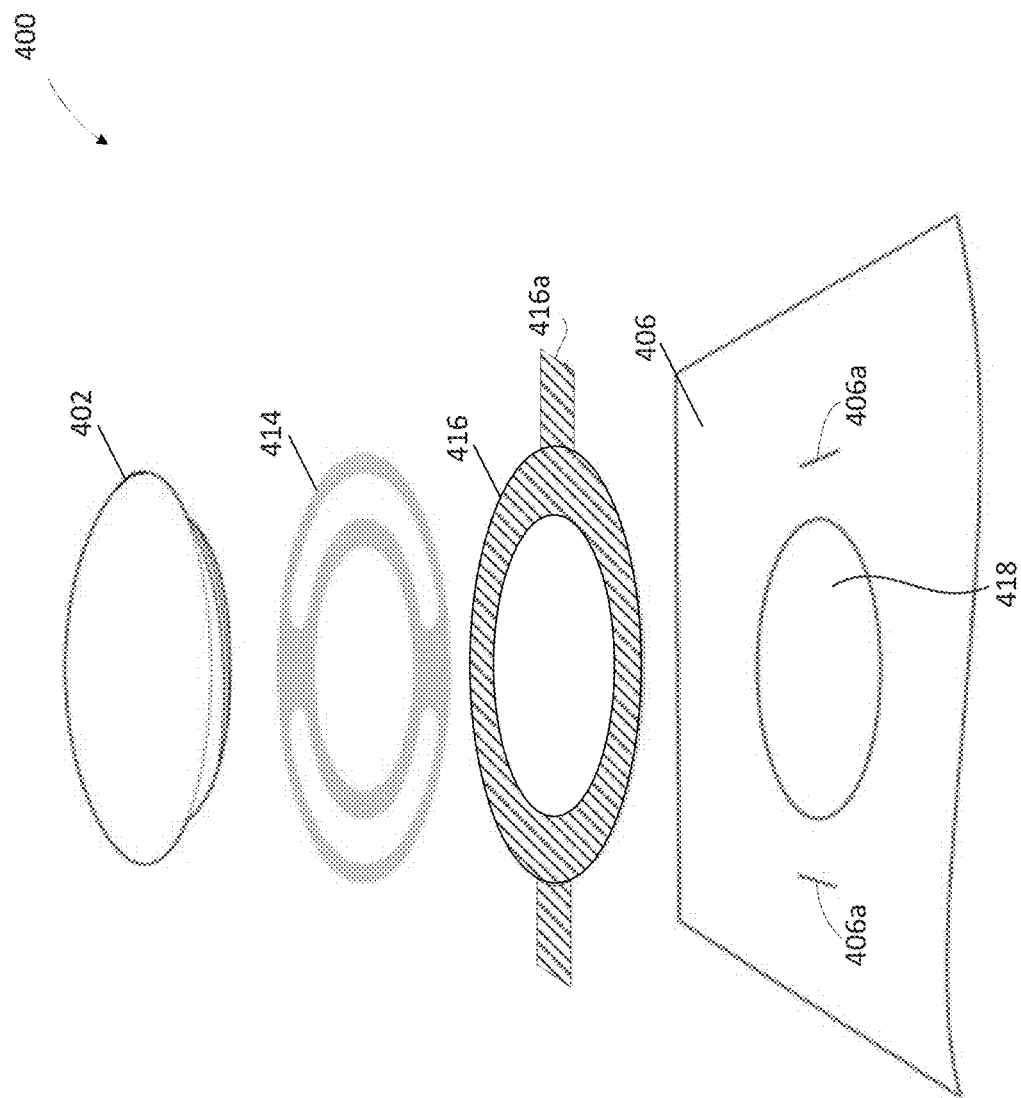
FIG. 4 is an exploded view of a computing node seat, in accordance with some embodiments.

FIG. 4 is an exploded view of a computing node seat, in accordance with some embodiments. Diagram 400 shows a computing node 402, a base bonding material 414, a base conductive fabric 416 having system leads 416a, and an underlying garment fabric 406. In embodiments, these may be similar to, respectively, computing node 202 of FIG. 2, base modeling material 314, base conductive fabric 316, system leads 316a, and fabric 306 of FIG. 3.

In embodiments, slits 406a may be cut or otherwise made into garment fabric 406 to facilitate the connection of system leads 416a to conductive fabric, conductive thread, or one or more wires (not shown) in the garment fabric 406. A hole 418, which may be similar to hole 318 of FIG. 3, may be inserted into the garment fabric 406 to align with the holes in the base bonding material 414 and/or the base conductive fabric 416.

In embodiments, a computing node seat may contain other layers of material in various order of layering.

Figure 5:
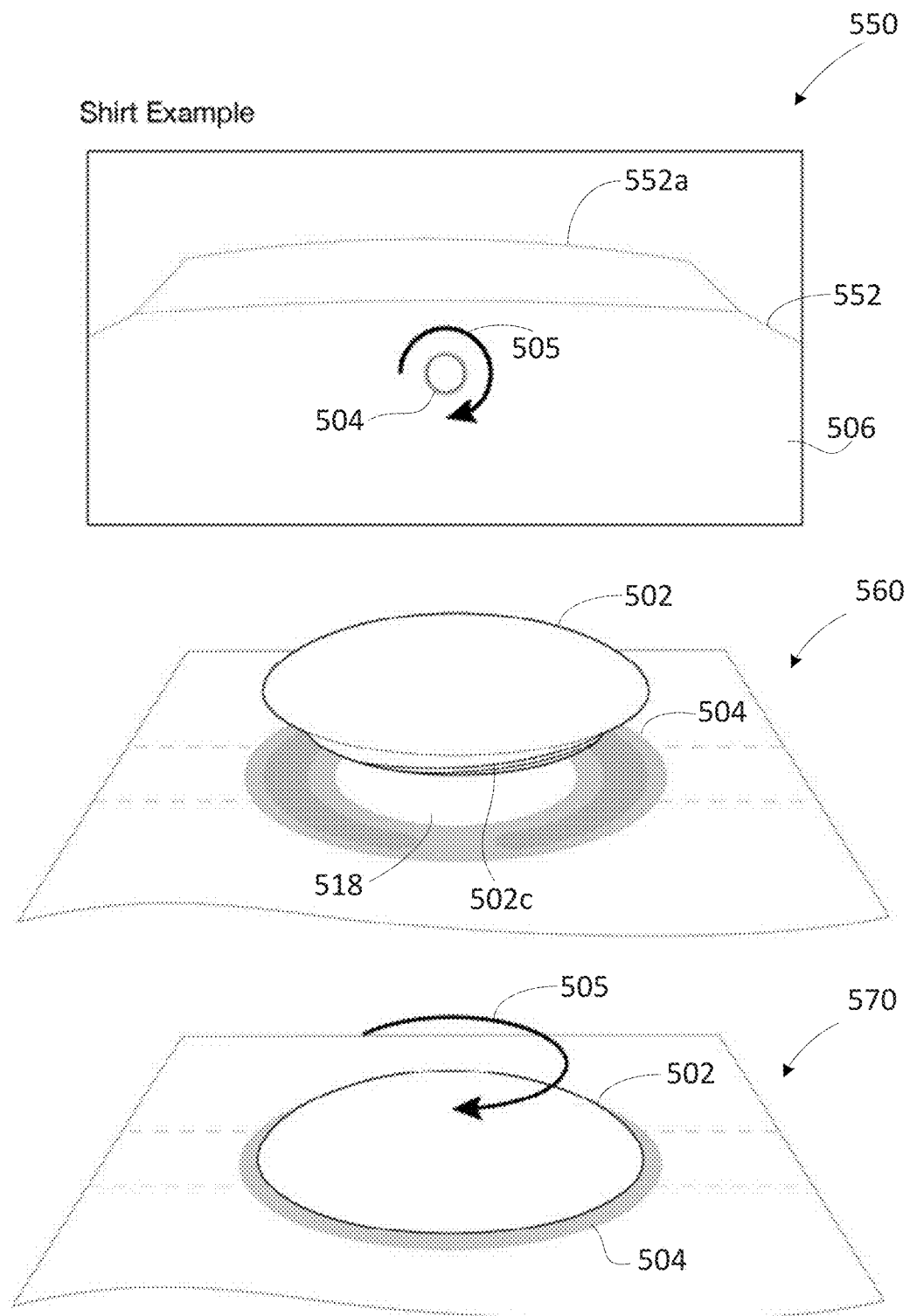
FIG. 5 illustrates a sequence of installing a computing node into a computing node seat that is part of a garment, in accordance with some embodiments.

FIG. 5 illustrates a sequence of installing a computing node into a computing node seat that is part of a garment, in accordance with some embodiments. Diagram 550 shows an example of the backside of a shirt 552 having shirt collar 552a. A computing node seat 504, which may be similar to computing node seat 204 of FIG. 2, may be attached to the back of the shirt 552 and integrated within the shirt garment 506, which may be similar to garment 206 of FIG. 2. A computing node 502 may be inserted into the computing node seat 504 in a clockwise direction 505.

Diagram 560 shows the computing node 502 about to be inserted into the computing node seat 504. The threaded portion 502c, which may be similar to the threaded portion 202c of FIG. 2, is shown to be inserted in the computing node seat hole 518, which may be similar to computing node seat hole 318 of FIG. 3.

Diagram 570 shows the computing node 502, after being turned in the tightening direction 505, to be completely seated in the computing node seat 504. At this point, the computing node 502 may be electrically coupled with the computing node seat 504, and may be receiving signals from one or more sensors (not shown) within the garment fabric 506.

Figure 6:
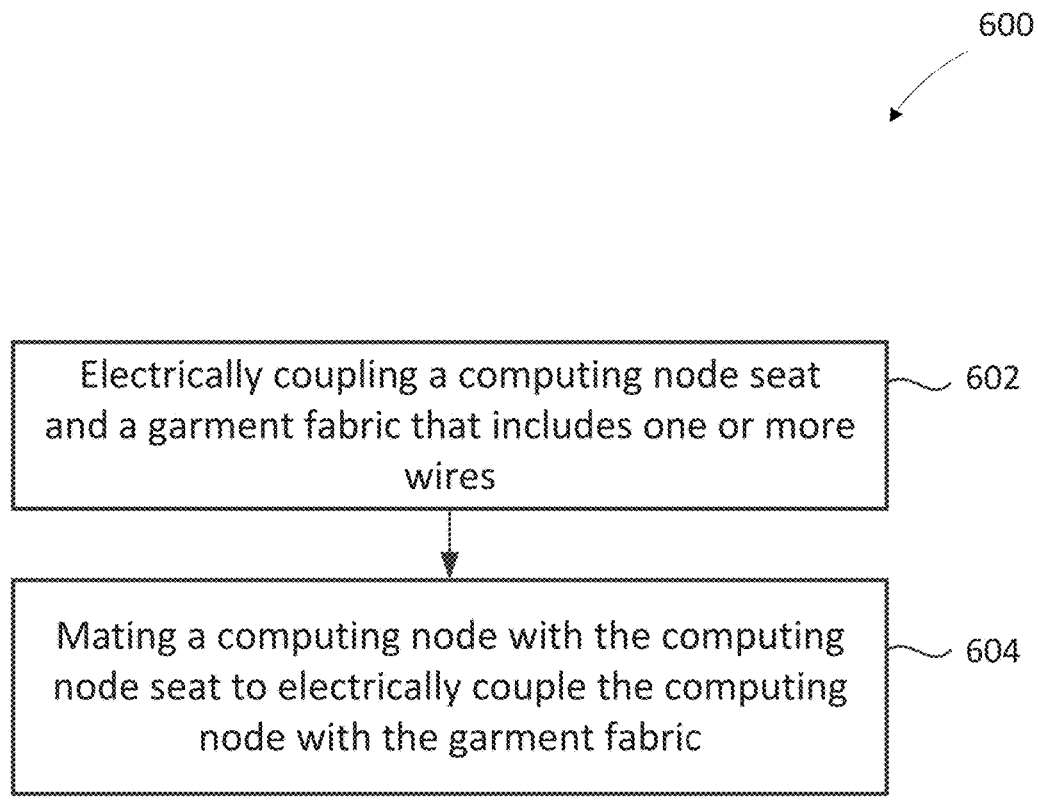
FIG. 6 illustrates a block diagram of a process for installing a computing node into a computing node seat, in accordance with some embodiments.

FIG. 6 illustrates a block diagram of a process for installing a computing node into a computing node seat, in accordance with some embodiments. Process 600 may be implemented using the computing node seat 104, 204, 304, and/or diagrams 400, 550, 560, 570 of FIGS. 1-5; computing node 101, 201, 402, 502 of FIGS. 1-2 and 4-5; and/or garment 106, 206, 306, 406, 506 of FIGS. 1-5.

At block 602, the process may include electrically coupling a computing node seat and a garment fabric that includes conductive fabric, conductive thread, or one or more wires. In embodiments, the computing node seat may be similar to the computing node seat 104 of FIG. 1, 204 of FIG. 2, 304 of FIG. 3, or 504 of FIG. 5. The computing node seat may be separately manufactured and coupled with the garment fabric, such as garment fabric 406 of FIG. 4, for example, by sewing, by overlaying the computing node seat on the garment fabric, or by otherwise attaching the computing node seat to the garment fabric.

At block 604, the process may include mating a computing node with the computing node seat to electrically couple the computing node with the garment fabric. In embodiments where the computer node seat may include two halves that are joined, such as 101 of FIG. 1, the first housing 102a and the second housing 102b may be attached together and on either side of the computing node seat 104. In embodiments where the computer node may include a single housing, such as housing 202 of FIG. 2, the computing node 202 may be inserted into the computing node seat 204. In embodiments, this insertion may include rotational insertion (screwing in), pushing in, snapping, and/or otherwise interlocking the computing node 202 into the computing node seat 204.

The corresponding structures, material, acts, and equivalents of all means or steps plus function elements in the claims below are intended to include any structure, material or act for performing the function in combination with other claimed elements are specifically claimed. The description of the present disclosure has been presented for purposes of illustration and description, but is not intended to be exhaustive or limited to the disclosure in the form disclosed. Many modifications and variations will be apparent to those of ordinary skill without departing from the scope and spirit of the disclosure. The embodiment was chosen and described in order to best explain the principles of the disclosure and the practical application, and to enable others of ordinary skill in the art to understand the disclosure for embodiments with various modifications as are suited to the particular use contemplated.

EXAMPLES

Examples, according to various embodiments, may include the following.

Example 1 may be a fabric article, comprising: a fabric having one or more embedded conductive wires; a computer node seat integrated into the fabric that includes: a base conductive fabric; and one or more system leads coupled to the base conductive fabric to electrically couple a computer node removably seated in the computer node seat with the one or more embedded wires in the fabric; wherein the computer node seat has a thickness substantially similar to the thickness of the fabric, or a flexibility substantially similar to the flexibility of the fabric, and is substantially flat.

Example 2 may include the fabric article of example 1, wherein the computer node seat further includes a bonding material applied to a surface of the base conductive fabric to secure the computer node to the computer node seat.

Example 3 may include the fabric article of example 1, wherein the computer node seat is integrated into the fabric.

Example 4 may include the fabric article of example 1, wherein the computer node seat or the fabric includes a sensor.

Example 5 may include the fabric article of example 4, wherein the fabric article is a garment, and the sensor is to track activity or to monitor a body of a person wearing the garment having the computer node seat with a removably seated computer node.

Example 6 may include the fabric article of example 1, wherein the base conductive fabric is stretchable.

Example 7 may include the fabric article of example 1, wherein the base conductive fabric is a light fabric such as Lycra™.

Example 8 may include the fabric article of example 1, wherein the fabric article is a tent or an awning.

Example 9 may include the fabric article of example 1, wherein the fabric is stretchable material.

Example 10 may include the fabric article of example 1, wherein the fabric is a light fabric such as Lycra™.

Example 11 may include the fabric article of any one of examples 1-10, further comprising: the removably seated computer node that includes: circuitry to process signals from the one or more wires of the fabric; a housing surrounding the circuitry; and a contact on an outer surface of the housing electrically coupled to the circuitry; wherein the contact of the removably seated computer node is electrically coupled to the one or more wires of the fabric and the housing is disposed both above and below a plane of the computer node seat.

Example 12 may include the fabric article of example 11, wherein a portion of the housing disposed below the plane of the computer node seat further includes male threading around the portion of the housing; and wherein the male threading is to facilitate rotational insertion of the portion of the enclosure below the plane of the fabric through a hole in the computer node seat to secure the housing to the node seat.

Example 13 may include the fabric article of example 11, wherein the housing has a first portion and a second portion that are detachable; and wherein the first portion is disposed on a first side of the computer node seat and the second portion is disposed on a second side of the computer node seat.

Example 14 may include the fabric article of example 11, wherein the computer node further includes a sensor.

Example 15 may include the fabric article of example 14, wherein the computer node sensor is to track activity or to monitor a body of a person wearing the fabric article.

Example 16 may include the fabric article of example 11, wherein the housing includes an indication of an orientation of the computer node.

Example 17 may include the apparatus of example 11, wherein the computer node is inductively charged.

Example 18 may include the apparatus of example 11, wherein at least a portion of the computer node passes through a hole in the computer node seat when seated in the computer node seat.

Example 19 may be a computer node apparatus comprising: circuitry to process signals from one or more wires of a fabric; a housing surrounding the circuitry; and a contact on an outer surface of the housing electrically coupled to the circuitry; wherein when the computer node is removably seated in a computer node seat, the contact is electrically coupled to the one or more wires of the fabric and the housing is disposed both above and below a plane of the node seat.

Example 20 may be the apparatus of example 19, wherein a portion of the housing disposed below the plane of the computer node seat further includes male threading around the portion of the housing; and wherein the male threading is to facilitate rotational insertion of the portion of the enclosure below the plane of the fabric through a hole in the computer node seat to secure the housing to the node seat.

Example 21 may include the apparatus of example 19, wherein the housing has a first portion and a second portion that are detachable; and wherein the first portion is disposed on a first side of the computer node seat and the second portion is disposed on a second side of the computer node seat.

Example 22 may include the apparatus of example 19, wherein the computer node includes a sensor.

Example 23 may include the apparatus of example 22, wherein the computer node sensor is to track activity or to monitor a body of a person wearing the computer node sensor.

Example 24 may include the apparatus of example 19, wherein the housing includes an indication of an orientation of the computer node.

Example 25 may include the apparatus of example 19, wherein the computer node is inductively charged.

Example 26 may include the apparatus of any one of examples 19-25, wherein at least a portion of the computer node passes through a hole in the computer node seat when seated in the computer node seat.

Example 27 may be a method comprising: electrically coupling a computer node seat and a fabric; and mating a computing node with the computing node seat to electrically couple the computing node with the fabric.

Example 28 may include the method of example 27, wherein mating the computing node further includes: if the computing node has a first housing part and a second housing part then positioning the first housing part on a first side of the computing node, positioning the second housing part on a second side of the computing node, and coupling the first and second housing parts together to secure and to electrically couple the computing node to the computing node seat; and if the computing node is a single housing then coupling the computing node to the computing node seat to secure and to electrically couple the computing node to the computing node seat.

Example 29 may include the method of example 28, wherein coupling the first and second housing parts together further includes screwing the first and the second housing parts together.

Example 30 may include the method of example 28, wherein coupling the first and second housing parts together further includes snapping the first and the second housing parts together.

Example 31 may include the method of example 28, wherein coupling the first and second housing parts together further includes interlocking the first and the second housing parts together.

Example 32 may include the method of any one of examples 28-31, wherein coupling the computing node to the computing node seat further includes screwing the computing node into a hole of the computing node seat.

Example 33 may be an apparatus comprising: means for electrically coupling a computing node seat and a fabric; and means for mating a computing node with the computing node seat to electrically couple the computing node with the fabric.

Example 34 may include the apparatus of example 33, wherein mating the computing node further includes: if the computing node has a first housing part and a second housing part then means for positioning the first housing part on a first side of the computing node, means for positioning the second housing part on a second side of the computing node, and means for coupling the first and second housing parts together to secure and to electrically couple the computing node to the computing node seat; and if the computing node is a single housing then means for coupling the computing node to the computing node seat to secure and to electrically couple the computing node to the computing node seat.

Example 35 may be the apparatus of example 34, wherein means for coupling the first and second housing parts together further includes means for screwing the first and the second housing parts together.

Example 36 may be the apparatus of example 34, wherein means for coupling the first and second housing parts together further includes means for snapping the first and the second housing parts together.

Example 37 may be the apparatus of example 34, wherein means for coupling the first and second housing parts together further includes means for interlocking the first and the second housing parts together.

Example 38 may be the apparatus of any one of examples 34-37, wherein means for coupling the computing node to the computing node seat further includes means for screwing the computing node into a hole of the computing node seat.

What is claimed is:

1. A fabric article, comprising: a fabric having one or more embedded conductive wires; a computer node seat integrated into the fabric that includes: a base conductive fabric; and
one or more system leads coupled to the base conductive fabric to electrically couple a computer node removably seated in the computer node seat with the one or more embedded wires in the fabric; and
wherein the computer node seat has a thickness substantially similar to the thickness of the fabric, or a flexibility substantially similar to the flexibility of the fabric, and is substantially flat; wherein the computer node includes a housing, wherein a lower portion of the housing includes a male threading around surrounding the lower portion threading is a part of the housing; and wherein the male threading is to facilitate rotational insertion of the lower portion of the housing through a hole in the computer node seat to secure the housing to the computer node seat.

2. The fabric article of claim 1, wherein the computer node seat further includes a bonding material applied to a surface of the base conductive fabric to secure the computer node to the computer node seat.

3. The fabric article of claim 1, wherein the computer node seat is integrated into the fabric.

4. The fabric article of claim 1, wherein the computer node seat or the fabric includes a sensor.

5. The fabric article of claim 4, wherein the fabric article is a garment, and the sensor is to track activity or to monitor a body of a person wearing the garment having the computer node seat with a removably seated computer node.

6. The fabric article of claim 1, wherein the base conductive fabric is stretchable.

7. The fabric article of claim 1, wherein the base conductive fabric is a light fabric such as Lycra™.

8. The fabric article of claim 1, wherein the fabric article is a tent or an awning.

9. The fabric article of claim 1, wherein the fabric is stretchable material.

10. The fabric article of claim 1, wherein the fabric is a light fabric such as Lycra™.

11. The fabric article of claim 1, wherein the housing has a first portion and a second portion that are detachable; and wherein the first portion is disposed on a first side of the computer node seat and the second portion is disposed on a second side of the computer node seat.

12. The fabric article of claim 1, wherein the computer node is inductively charged.

13. The fabric article of claim 1, wherein at least a portion of the computer node passes through a hole in the computer node seat when seated in the computer node seat.

14. A computer node apparatus comprising: circuitry to process signals from one or more wires of a fabric; a housing surrounding the circuitry; and a contact on an outer surface of the housing electrically coupled to the circuitry; wherein when the computer node is removably seated in a computer node seat, the contact is electrically coupled to the one or more wires of the fabric and the housing is disposed both above and below a plane of the node seat; wherein a lower portion of the housing is to be disposed below the plane of the computer node seat;
wherein threading is a part of further includes a male threading around surrounding the lower portion of the housing; and wherein the male threading is to facilitate rotational insertion of the lower portion of the enclosure housing below the plane of the fabric through a hole in the computer node seat to secure the housing to the node seat.

15. The apparatus of claim 14, wherein the housing has a first portion and a second portion that are detachable; and wherein the first portion is disposed on a first side of the computer node seat and the second portion is disposed on a second side of the computer node seat.

16. A method comprising: electrically coupling a computing node seat and a fabric; mating a computing node with the computing node seat to physically secure and to electrically couple the computing node with the fabric, wherein the computing node includes a surrounded single housing, wherein threading is a part that includes a male threading around surrounding a lower the portion of the housing to facilitate rotational insertion of the lower portion of the housing below a plane of the fabric through a hole in the computing node seat to secure the computing node to the node seat.

17. The method of claim 16, wherein mating the computing node to the computing node seat further includes rotationally inserting the housing into the hole in the computing node seat.

* * * * *

UNITED STATES PATENT AND TRADEMARK OFFICE
CERTIFICATE OF CORRECTION

PATENT NO. : 10,310,558 B2
APPLICATION NO. : 15/496512
DATED : June 4, 2019
INVENTOR(S) : Eric Lewallen Page 1 of 2

It is certified that error appears in the above-identified patent and that said Letters Patent is hereby corrected as shown below:

In the Claims

At Column 11, Line 2 cancel the text beginning "1. A fabric article, comprising:" to and ending "through a hole in the computer node seat to secure the housing to the computer node seat." in Column 11, Line 20 and insert the following claim:

--1. A fabric article, comprising: a fabric having one or more embedded conductive wires; a computer node seat integrated into the fabric that includes:
    a base conductive fabric; and
    one or more system leads coupled to the base conductive fabric to electrically couple a computer node removably seated in the computer node seat with the one or more embedded wires in the fabric; and
    wherein the computer node seat has a thickness substantially similar to the thickness of the fabric, or a flexibility substantially similar to the flexibility of the fabric, and is substantially flat; wherein the computer node includes a housing, wherein a lower portion of the housing includes a male threading surrounding the lower portion of the housing; and wherein the male threading is to facilitate rotational insertion of the lower portion of the housing through a hole in the computer node seat to secure the housing to the computer node seat.--

At Column 12, Line 8 cancel the text beginning "14. A computer node apparatus comprising:" to and ending "to secure the housing to the node seat." in Column 12, Line 24 and insert the following claim:

--14. A computer node apparatus comprising: circuitry to process signals from one or more wires of a fabric; a housing surrounding the circuitry; and a contact on an outer surface of the housing electrically coupled to the circuitry; wherein when the computer node is removably seated in a computer node seat, the contact is electrically coupled to the one or more wires of the fabric and the housing is disposed both above and below a plane of the node seat;

Signed and Sealed this
Second Day of June, 2020

Andrei Iancu
*Director of the United States Patent and Trademark Office* wherein a lower portion of the housing is to be disposed below the plane of the computer node seat;
further includes a male threading surrounding the lower portion of the housing; and
wherein the male threading is to facilitate rotational insertion of the lower portion of the housing below the plane of the fabric through a hole in the computer node seat to secure the housing to the node seat.--

At Column 12, Line 30 cancel the text beginning "16. A method comprising:" to and ending "to secure the computing node to the node seat." in Column 12, Line 40 and insert the following claim:

--16. A method comprising:
electrically coupling a computing node seat and a fabric;
mating a computing node with the computing node seat to physically secure and to electrically couple the computing node with the fabric, wherein the computing node includes a surrounded single housing, that includes a male threading surrounding a lower portion of the housing to facilitate rotational insertion of the lower portion of the housing below a plane of the fabric through a hole in the computing node seat to secure the computing node to the node seat.--